US010530177B2

(12) United States Patent
Meskens et al.

(10) Patent No.: US 10,530,177 B2
(45) Date of Patent: Jan. 7, 2020

(54) MULTI-LOOP IMPLANT CHARGER

(71) Applicant: Cochlear Limited, Macquarie University, NSW (AU)

(72) Inventors: Werner Meskens, Opwijk (BE); Oliver Ridler, Sydney (AU)

(73) Assignee: Cochlear Limited, Macquarie University (AU)

( * ) Notice: Subject to any disclaimer, the term of this patent is extended or adjusted under 35 U.S.C. 154(b) by 98 days.

(21) Appl. No.: 15/454,105

(22) Filed: Mar. 9, 2017

(65) Prior Publication Data

US 2018/0262037 A1    Sep. 13, 2018

(51) Int. Cl.
| | |
|---|---|
| H02J 7/02 | (2016.01) |
| H02J 7/10 | (2006.01) |
| H02J 50/10 | (2016.01) |
| H02J 50/40 | (2016.01) |
| A61N 1/378 | (2006.01) |

(52) U.S. Cl.
CPC ............ *H02J 7/025* (2013.01); *A61N 1/3787* (2013.01); *H02J 50/10* (2016.02); *H02J 50/40* (2016.02)

(58) Field of Classification Search
CPC . H02J 7/025; H02J 50/10; H02J 50/40; A61N 1/36036; A61N 1/3787
USPC .......................................... 320/108; 307/104
See application file for complete search history.

(56) References Cited

U.S. PATENT DOCUMENTS

| | | | |
|---|---|---|---|
| 649,621 A | 5/1900 | Tesla | |
| 3,600,669 A * | 8/1971 | McClain | G01L 9/007 340/870.35 |
| 4,556,886 A * | 12/1985 | Shimizu | G01D 5/243 324/166 |
| 5,519,262 A | 5/1996 | Wood | |
| 5,898,578 A * | 4/1999 | Tamura | H02J 5/005 363/19 |
| 6,028,413 A * | 2/2000 | Brockmann | H02J 7/025 320/108 |
| 6,212,430 B1 | 4/2001 | Kung | |
| 6,291,968 B1 * | 9/2001 | Nantz | H02J 7/0054 320/108 |

(Continued)

FOREIGN PATENT DOCUMENTS

| | | | |
|---|---|---|---|
| JP | 2018014864 A | * | 1/2018 |
| WO | WO-2017026721 A1 | * | 2/2017 |

OTHER PUBLICATIONS

"Design of Inductive Wireless Power Systems for Consumer Electronics", www.cornetwipos.org, DraMCo (Belgium) & Fraunhofer IZM (Germany), Sep. 2014, 33 pages.

(Continued)

*Primary Examiner* — Robert Grant
*Assistant Examiner* — John T Trischler
(74) *Attorney, Agent, or Firm* — Edell, Shapiro & Finnan, LLC

(57) ABSTRACT

Techniques for charging a battery within an implantable component (implant) of an implantable medical device system. A multi-loop external charging device includes a plurality of coil/loop antennas that are each configured to emit a magnetic field that is received by an implantable coil of the implantable component. At least one characteristic (e.g., phases, amplitudes, etc.) of the emitted magnetic fields are varied relative to one another over time.

19 Claims, 15 Drawing Sheets

(56) References Cited

U.S. PATENT DOCUMENTS

| | | | | |
|---|---|---|---|---|
| 6,366,051 B1* | 4/2002 | Nantz | H02J 7/0054 | 320/108 |
| 6,442,434 B1* | 8/2002 | Zarinetchi | A61N 1/3787 | 607/61 |
| 6,650,213 B1 | 11/2003 | Sakurai et al. | | |
| 6,724,607 B2* | 4/2004 | Hayashi | H02N 2/147 | 310/316.01 |
| 7,042,196 B2 | 5/2006 | Ka-Lai et al. | | |
| 7,107,103 B2 | 9/2006 | Schulman et al. | | |
| 7,248,017 B2* | 7/2007 | Cheng | H01F 38/14 | 320/108 |
| 7,634,318 B2* | 12/2009 | Tran | A61N 1/3787 | 607/61 |
| 7,932,696 B2* | 4/2011 | Peterson | A61N 1/3787 | 320/114 |
| 8,044,635 B2* | 10/2011 | Peterson | A61N 1/3787 | 320/114 |
| 8,125,188 B2* | 2/2012 | Doll | H02J 7/0024 | 320/134 |
| 8,278,871 B2* | 10/2012 | Kallmyer | A61N 1/3787 | 320/108 |
| 8,340,778 B2* | 12/2012 | Tran | A61N 1/3787 | 607/61 |
| 8,457,547 B2* | 6/2013 | Meskens | H04B 5/0075 | 370/310 |
| 8,541,975 B2* | 9/2013 | Park | H02J 7/025 | 320/108 |
| 8,598,841 B2* | 12/2013 | Peterson | A61N 1/3787 | 320/114 |
| 8,612,013 B2* | 12/2013 | Forsell | A61N 1/3787 | 607/60 |
| 8,629,576 B2* | 1/2014 | Levine | H02J 5/005 | 307/104 |
| 8,847,548 B2* | 9/2014 | Kesler | H02J 50/70 | 320/108 |
| 8,855,554 B2* | 10/2014 | Cook | H02J 5/005 | 455/41.1 |
| 8,878,393 B2* | 11/2014 | Kirby | H04B 5/0037 | 307/104 |
| 8,890,470 B2* | 11/2014 | Partovi | H01F 7/0252 | 320/108 |
| 8,896,264 B2* | 11/2014 | Partovi | H01F 7/0252 | 320/108 |
| 8,901,881 B2* | 12/2014 | Partovi | H01F 7/0252 | 320/108 |
| 8,947,045 B2* | 2/2015 | Jung | H02J 7/0029 | 320/108 |
| 8,965,523 B2* | 2/2015 | Forsell | A61N 1/3787 | 607/60 |
| 9,089,717 B2* | 7/2015 | Forsell | A61B 34/20 | |
| 9,161,140 B2* | 10/2015 | Meskens | H04R 3/08 | |
| 9,184,632 B2* | 11/2015 | Kirby | G06K 7/0008 | |
| 9,250,705 B2* | 2/2016 | Richter | G06F 3/016 | |
| 9,312,924 B2* | 4/2016 | Ozaki | H02J 7/025 | |
| 9,356,473 B2* | 5/2016 | Ghovanloo | H02J 5/005 | |
| 9,391,463 B2* | 7/2016 | Jung | H02J 5/005 | |
| 9,461,714 B2* | 10/2016 | Cook | H02J 5/005 | |
| 9,472,338 B2* | 10/2016 | Keeling | H02J 50/12 | |
| 9,498,635 B2* | 11/2016 | Dellamano | A61N 1/3787 | |
| 9,566,448 B2* | 2/2017 | Forsell | A61B 34/20 | |
| 9,579,510 B2* | 2/2017 | Meskens | A61N 1/37217 | |
| 9,595,834 B2* | 3/2017 | Yamamoto | G01V 3/10 | |
| 9,685,792 B2* | 6/2017 | Yang | H01F 27/28 | |
| 9,707,406 B1* | 7/2017 | Dellamano | H04B 5/0031 | |
| 9,713,726 B1* | 7/2017 | Dellamano | H04B 5/0031 | |
| 9,716,440 B2* | 7/2017 | Kaeriyama | H04B 3/50 | |
| 9,717,917 B2* | 8/2017 | Dellamano | H04B 5/0031 | |
| 9,731,141 B2* | 8/2017 | Tran | A61N 1/3787 | |
| 9,735,589 B2* | 8/2017 | Goma | H02J 5/005 | |
| 9,757,575 B2* | 9/2017 | Dellamano | H04B 5/0031 | |
| 9,784,878 B2* | 10/2017 | Yamamoto | G01V 3/104 | |
| 9,818,532 B2* | 11/2017 | Hatanaka | H04B 5/0037 | |
| 9,821,155 B2* | 11/2017 | Leigh | A61N 1/0541 | |
| 9,833,629 B2* | 12/2017 | Dellamano | H04B 5/0031 | |
| 9,839,788 B2* | 12/2017 | Dellamano | H04B 5/0031 | |
| 9,854,370 B2* | 12/2017 | Meskens | A61N 1/37217 | |
| 9,948,142 B2* | 4/2018 | Tseng | H02J 7/0042 | |
| 10,009,069 B2* | 6/2018 | Kerselaers | H04B 5/0037 | |
| 10,020,683 B2* | 7/2018 | Carobolante | H02J 5/005 | |
| 10,022,549 B2* | 7/2018 | Dellamano | H04B 5/0031 | |
| 10,083,792 B2* | 9/2018 | Werner | H01F 27/365 | |
| 10,090,711 B2* | 10/2018 | Shimokawa | H02J 5/005 | |
| 10,141,766 B2* | 11/2018 | Zhang | H02J 7/0027 | |
| 2002/0027424 A1* | 3/2002 | Nantz | H02J 7/0054 | 320/108 |
| 2002/0053858 A1* | 5/2002 | Hayashi | H02N 2/147 | 310/316.01 |
| 2003/0078634 A1* | 4/2003 | Schulman | A61N 1/08 | 607/61 |
| 2004/0066093 A1* | 4/2004 | Hanson | H02J 3/01 | 307/11 |
| 2005/0140482 A1* | 6/2005 | Cheng | H01F 38/14 | 336/180 |
| 2006/0076922 A1* | 4/2006 | Cheng | H01F 38/14 | 320/108 |
| 2008/0288025 A1* | 11/2008 | Peterson | A61N 1/3787 | 607/60 |
| 2009/0038623 A1* | 2/2009 | Farbarik | A61F 2/02 | 128/848 |
| 2009/0243397 A1* | 10/2009 | Cook | H02J 5/005 | 307/104 |
| 2010/0044120 A1* | 2/2010 | Richter | G06F 3/016 | 178/18.01 |
| 2010/0328044 A1* | 12/2010 | Waffenschmidt | H02J 7/025 | 340/10.4 |
| 2011/0009925 A1* | 1/2011 | Leigh | A61N 1/37229 | 607/60 |
| 2011/0043051 A1* | 2/2011 | Meskens | H04B 5/0075 | 307/104 |
| 2011/0062914 A1* | 3/2011 | Park | H02J 7/025 | 320/106 |
| 2011/0074349 A1* | 3/2011 | Ghovanloo | H02J 5/005 | 320/108 |
| 2011/0172742 A1* | 7/2011 | Peterson | A61N 1/3787 | 607/61 |
| 2011/0193688 A1* | 8/2011 | Forsell | A61B 34/20 | 340/10.4 |
| 2011/0196452 A1* | 8/2011 | Forsell | A61N 1/3787 | 607/60 |
| 2012/0019201 A1* | 1/2012 | Peterson | A61N 1/3787 | 320/108 |
| 2012/0146576 A1* | 6/2012 | Partovi | H01F 7/0252 | 320/108 |
| 2012/0169139 A1* | 7/2012 | Kudo | H02J 5/005 | 307/104 |
| 2012/0193993 A1* | 8/2012 | Azancot | H02J 5/005 | 307/104 |
| 2012/0242285 A1* | 9/2012 | Jung | H02J 7/0029 | 320/108 |
| 2013/0023954 A1* | 1/2013 | Meskens | A61N 1/37217 | 607/57 |
| 2013/0093389 A1* | 4/2013 | Partovi | H01F 7/0252 | 320/108 |
| 2013/0099735 A1* | 4/2013 | Partovi | H01F 7/0252 | 320/108 |
| 2013/0300205 A1 | 11/2013 | Tzanidis et al. | | |
| 2013/0335019 A1* | 12/2013 | Katsumata | H01M 10/443 | 320/108 |
| 2013/0342025 A1* | 12/2013 | Cook | H02J 5/005 | 307/104 |
| 2014/0021798 A1* | 1/2014 | Kesler | H01F 38/14 | 307/104 |
| 2014/0070764 A1* | 3/2014 | Keeling | H02J 50/12 | 320/108 |
| 2014/0073237 A1* | 3/2014 | Meskens | H04B 5/0075 | 455/7 |
| 2014/0176063 A1* | 6/2014 | Forsell | A61N 1/3787 | 320/108 |

(56) References Cited

U.S. PATENT DOCUMENTS

| | | | | |
|---|---|---|---|---|
| 2014/0184155 | A1* | 7/2014 | Cha | H02J 7/025 320/109 |
| 2014/0253052 | A1* | 9/2014 | Goma | H02J 5/005 320/166 |
| 2014/0266031 | A1* | 9/2014 | Sasaki | H01F 38/14 320/108 |
| 2014/0300197 | A1* | 10/2014 | Wakabayashi | H01F 38/14 307/104 |
| 2014/0325830 | A1* | 11/2014 | Hatanaka | H02J 7/025 29/602.1 |
| 2014/0375256 | A1* | 12/2014 | Lee | H02J 5/005 320/108 |
| 2015/0022147 | A1* | 1/2015 | Jung | H02J 5/005 320/108 |
| 2015/0042271 | A1* | 2/2015 | Nakagawa | H02J 7/025 320/108 |
| 2015/0115727 | A1* | 4/2015 | Carobolante | H02J 5/005 307/104 |
| 2015/0130412 | A1* | 5/2015 | Partovi | H01F 7/0252 320/108 |
| 2015/0217648 | A1* | 8/2015 | Ichikawa | H02J 7/025 320/108 |
| 2015/0244199 | A1* | 8/2015 | Chen | H04B 5/0037 320/108 |
| 2015/0255987 | A1 | 9/2015 | Yang et al. | |
| 2015/0311725 | A1* | 10/2015 | Yamamoto | G01V 3/104 307/104 |
| 2015/0318896 | A1* | 11/2015 | Kerselaers | H04B 5/02 455/41.1 |
| 2015/0326061 | A1* | 11/2015 | Davison | H02J 7/0044 320/108 |
| 2015/0328469 | A1* | 11/2015 | Forsell | A61B 34/20 607/61 |
| 2015/0332845 | A1* | 11/2015 | Werner | H01F 27/365 307/104 |
| 2015/0349541 | A1* | 12/2015 | Yamamoto | G01V 3/10 307/104 |
| 2016/0094053 | A1* | 3/2016 | Shimokawa | H02J 5/005 307/104 |
| 2016/0094075 | A1* | 3/2016 | Tseng | H02J 50/10 320/108 |
| 2016/0114174 | A1* | 4/2016 | Colvin | A61N 1/3787 607/46 |
| 2016/0141908 | A1* | 5/2016 | Jakl | H02J 7/0004 320/108 |
| 2016/0164332 | A1 | 6/2016 | Elkhouly et al. | |
| 2016/0285317 | A1* | 9/2016 | Maniktala | H02J 50/12 |
| 2017/0126281 | A1* | 5/2017 | Cook | H02J 5/005 |
| 2017/0163096 | A1* | 6/2017 | Akahori | H02J 50/90 |
| 2017/0189693 | A1* | 7/2017 | Dellamano | H04B 5/0031 |
| 2017/0189695 | A1* | 7/2017 | Dellamano | H04B 5/0031 |
| 2017/0189696 | A1* | 7/2017 | Dellamano | H04B 5/0031 |
| 2017/0189697 | A1* | 7/2017 | Dellamano | H04B 5/0031 |
| 2017/0189698 | A1* | 7/2017 | Dellamano | H04B 5/0031 |
| 2017/0189699 | A1* | 7/2017 | Dellamano | H04B 5/0031 |
| 2017/0231717 | A1* | 8/2017 | Forsell | A61B 34/20 320/108 |
| 2017/0288739 | A1* | 10/2017 | Shin | H04B 5/0037 |
| 2017/0310236 | A1* | 10/2017 | Kaeriyama | H04B 3/50 |
| 2017/0359102 | A1* | 12/2017 | Park | H02J 7/00 |
| 2017/0363763 | A1* | 12/2017 | Yamamoto | G01V 3/104 |
| 2018/0048164 | A1* | 2/2018 | Zhang | H02J 7/0027 |
| 2018/0076636 | A1* | 3/2018 | Zhang | H02J 7/0027 |
| 2018/0178666 | A1* | 6/2018 | Javaid | B60L 11/1831 |
| 2018/0219400 | A1* | 8/2018 | Jin | H02J 7/02 |
| 2018/0248415 | A1* | 8/2018 | Yoshizawa | H02J 50/90 |
| 2018/0248416 | A1* | 8/2018 | Yoshizawa | H02J 50/90 |
| 2018/0269719 | A1* | 9/2018 | Yoshizawa | H02J 50/10 |
| 2018/0269720 | A1* | 9/2018 | Yoshizawa | H02J 50/10 |
| 2018/0272131 | A1* | 9/2018 | Meskens | A61N 1/3787 |
| 2019/0058347 | A1* | 2/2019 | Zhang | H02J 7/0027 |

OTHER PUBLICATIONS

International Search Report and Written Opinion in corresponding International Application No. PCT/IB2018/051403, dated Jun. 15, 2018, 7 pages.

* cited by examiner

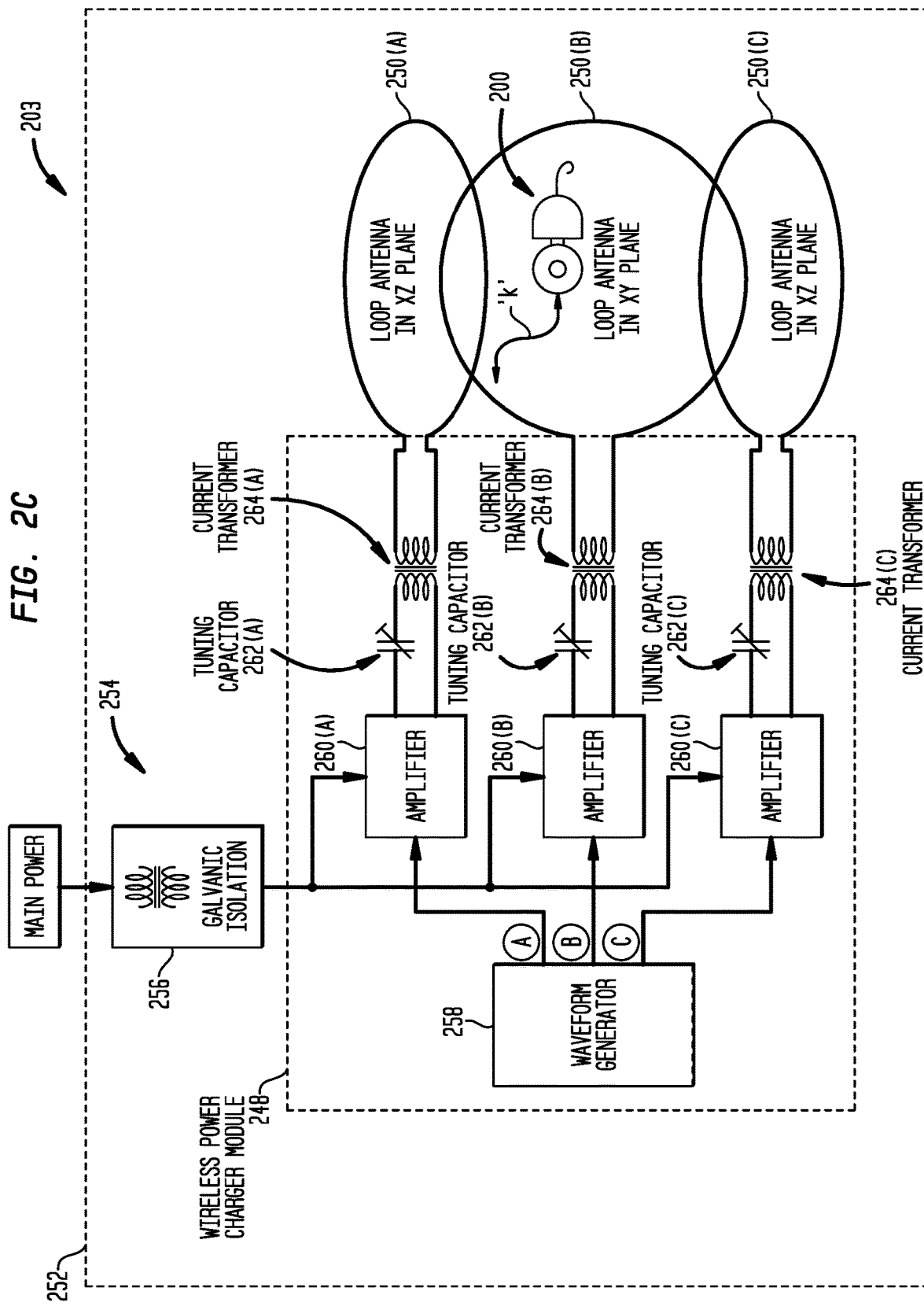

- 782 — DELIVERING A FIRST ALTERNATING CURRENT SIGNAL TO A FIRST COIL ANTENNA OF THE WIRELESS CHARGER SO AS TO PRODUCE A FIRST MAGNETIC FIELD

- 784 — DELIVERING A SECOND ALTERNATING CURRENT SIGNAL TO A SECOND COIL ANTENNA OF THE WIRELESS CHARGER SO AS TO PRODUCE A SECOND MAGNETIC FIELD, WHEREIN THE SECOND ALTERNATING CURRENT SIGNAL CAUSES AT LEAST ONE OF THE PHASE OR AMPLITUDE OF THE SECOND MAGNETIC FIELD TO VARY WITH RESPECT TO THE PHASE OR AMPLITUDE OF THE FIRST MAGNETIC FIELD

- 786 — RECEIVING, AT THE IMPLANTABLE COIL, A COMBINED MAGNETIC FIELD COMPRISED OF THE FIRST AND SECOND MAGNETIC FIELDS, WHEREIN THE COMBINED MAGNETIC FIELD GENERATES AN ALTERNATING CURRENT SIGNAL AT THE IMPLANTABLE COIL

880A

880B

880C

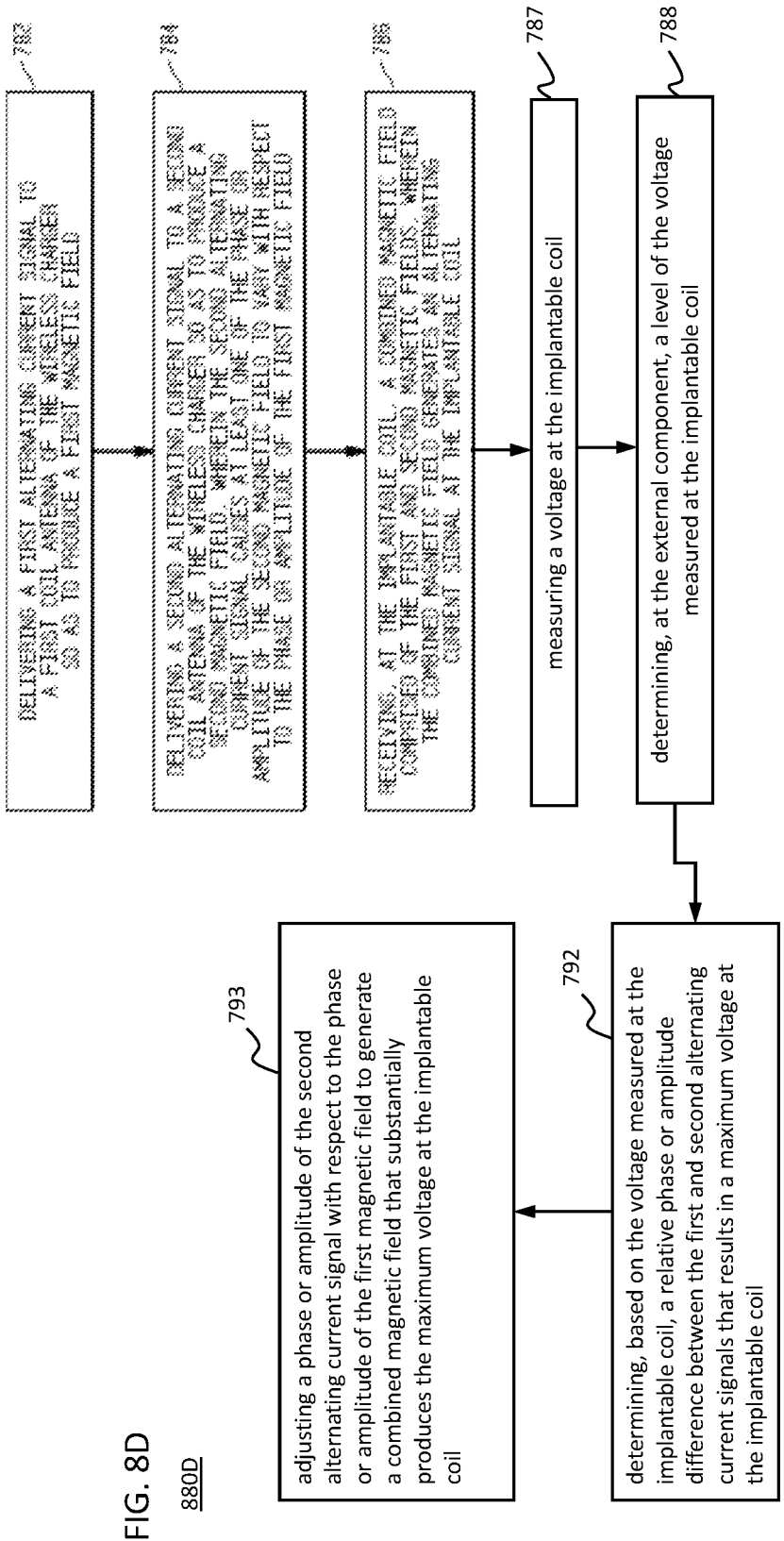

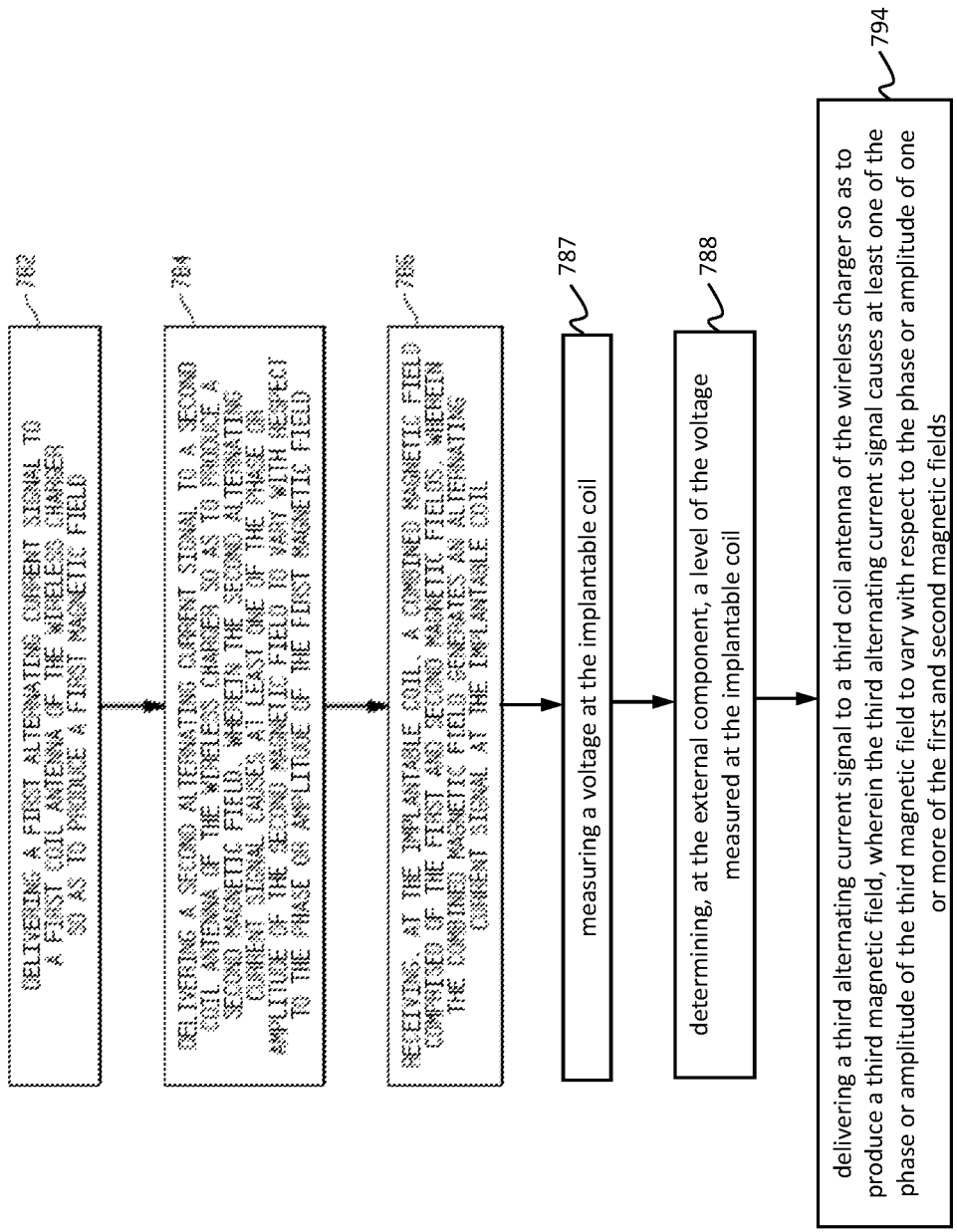

MULTI-LOOP IMPLANT CHARGER

BACKGROUND

Field of the Invention

The present invention relates generally to charging of implantable medical devices.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or are employed to investigate, replace or modify the anatomy or a physiological process. Many of these functional components utilize power and/or data received from external components that are part of, or operate in conjunction with, the implantable medical device.

SUMMARY

In one aspect a method for wireless transfer of power from a wireless charger to an implantable component having an implantable coil is provided. The method comprises: delivering a first alternating current signal to a first coil antenna of the wireless charger so as to produce a first magnetic field; delivering a second alternating current signal to a second coil antenna of the wireless charger so as to produce a second magnetic field, wherein the second alternating current signal causes at least one of the phase or amplitude of the second magnetic field to vary with respect to the phase or amplitude of the first magnetic field; and receiving, at the implantable coil, a combined magnetic field comprised of the first and second magnetic fields, wherein the combined magnetic field generates an alternating current signal at the implantable coil.

In another aspect an external charger device for an implantable medical device is provided. The external charger device comprises: at least first and second coil antennas configured to generate first and second magnetic fields, respectively; and a coil excitation system connected to the first and second coil antennas and configured to independently drive the first and second coil antennas so that at least one characteristic of the first magnetic field varies, over time, with respect to the same at least one characteristic of the second magnetic field.

In another aspect, an implantable medical device system is provided. The implantable medical device system comprises: an external charger including: at least first and second external coil antennas in close proximity to one another and configured to emit first and second magnetic fields that collectively generate a combined magnetic field having a combined magnetic field vector; and a coil excitation system connected to the first and second coil antennas and configured to drive the first and second coil antennas with time variant waveforms to cause fluctuation in an orientation of the combined magnetic field vector.

BRIEF DESCRIPTION OF THE DRAWINGS

Embodiments of the present invention are described herein in conjunction with the accompanying drawings, in which:

FIG. 2C is a schematic block diagram illustrating further details of the external charging device of FIG. 2B;

FIG. 7 is a flowchart of a method, in accordance with embodiments presented herein.

FIG. 8D is a flowchart of a method, in accordance with certain embodiments presented herein.

FIG. 8E is a flowchart of a method, in accordance with certain embodiments presented herein.

DETAILED DESCRIPTION

Presented herein are techniques for charging a battery within an implantable component (implant) of an implantable medical device system in a manner that substantially reduces the impact of dead charging zones (i.e., spatial areas in which no power is received by the implantable component). A multi-loop (multi-antenna) external charging device, sometimes referred to herein as an external or wireless charger, includes a plurality of external coil/loop antennas that are each configured to emit a magnetic field that is received by an implantable coil of the implantable component. At least one characteristic (e.g., phases, amplitudes, etc.) of the emitted magnetic fields are varied relative to one another over time. By varying at least one characteristic of the emitted magnetic fields relative to one another (i.e., varying the relative phase and/or relative amplitude differences between the emitted magnetic fields), the direction/orientation of the combined magnetic field vector also changes (e.g., rotates) over time and, accordingly, the location of the dead charging zones will also change over time. As a result, regardless of the relative locations of the external coil antennas and the implantable coil, the implantable coil will, at different times, have a non-zero amount of magnetic flux there through that induces a current in the implantable coil.

In addition, varying at least one characteristic of the emitted magnetic fields relative to one another enables the charger to operate without feedback from the implantable component (e.g., without data indicating the position of the implantable coil relative to the charger coils, the presence of a magnetic field from an implantable magnet, the induced voltage in the implant coil, etc.). As a result, the external charger can be an "open-loop" charger manufactured without a communications interface/circuitry to detect load modulation from the implant or can be a device that is configured to default to an "open-loop" configuration (i.e., to operate without feedback from the implant) in the absence of a communication signal from the implant (e.g. for backward compatibility, when interference prevents reliable data communication, etc.).

There are a number of different types of implantable medical device systems in which embodiments of the present invention may be implemented. However, merely for ease of illustration, the techniques presented herein are primarily described with reference to one type of implantable medical device system, namely a cochlear implant system. It is to be appreciated that the techniques presented herein may be used in any other partially or fully implantable medical device system now known or later developed, including other auditory prosthesis systems, such as systems that include auditory brainstem stimulators, electro-acoustic hearing prostheses, bimodal hearing prostheses, etc.

Figure 1:
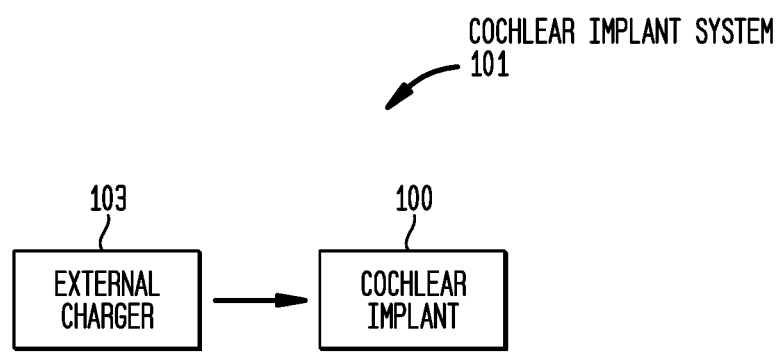
FIG. 1 is a block diagram illustrating a cochlear implant system, in accordance with embodiments presented herein.

FIG. 1 is a block diagram of an exemplary cochlear implants system 101 in which embodiments presented herein are implemented. The cochlear implant system 101 comprises an implantable component, referred to as cochlear implant 100, and an external charging device, sometimes referred to herein as a wireless or external charger 103. The external charger 103 may have a number of different forms, such as a pillow charger, charging mat, etc.

As described below, the cochlear implant 100 comprises a rechargeable battery (not shown in FIG. 1) that is configured to be recharged using power signals received from the external charger 103 via an inductive radio frequency (RF) link. Also as described below, the external charger 103 is a multi-loop (multi-antenna) device that includes two or more coil antennas (antenna loops) that each emit a magnetic field. The two or more coil antennas are driven such that the phases and/or amplitudes of the emitted magnetic fields vary (continuously or discontinuously), over time, relative to one another. As a result, the orientation of a summed magnetic field vector (corresponding to the summation of the emitted magnetic fields) changes (e.g., rotates) over time.

Figure 2A:
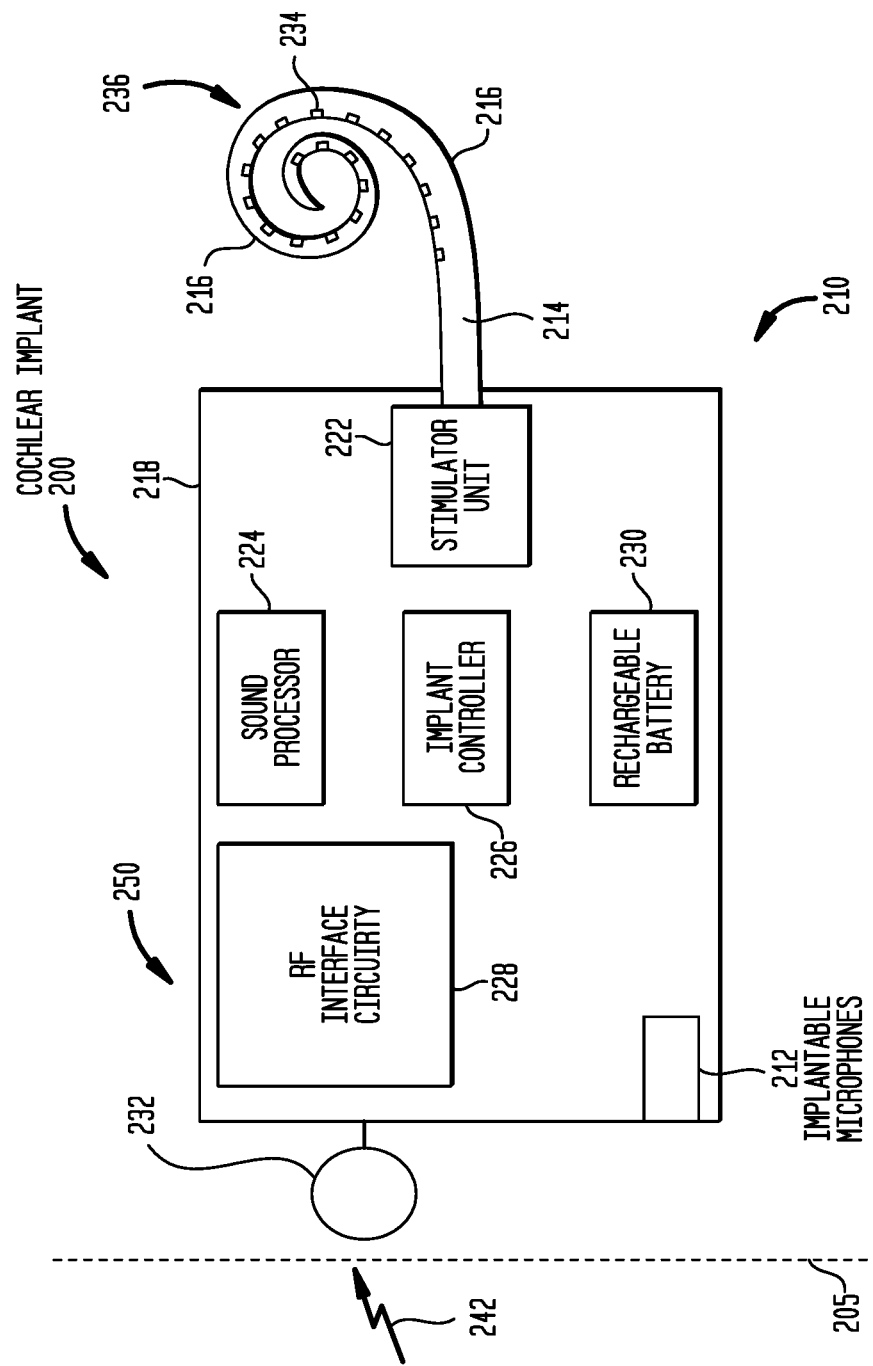
FIG. 2A is block diagram of a cochlear implant, in accordance with embodiments presented herein.

It is to be appreciated that the cochlear implant 100 of FIG. 1, as well as the external charger 103 of FIG. 1, may each have a number of different arrangements. FIG. 2A is a block diagram illustrating one example arrangement for the cochlear implant 100, referred to as cochlear implant 200.

The cochlear implant 200 is a totally implantable cochlear implant where all components of the cochlear implant are configured to be implanted under the skin/tissue 205 of a recipient. Because all components are implantable, cochlear implant 200 operates, for at least a finite period of time, without the presence of an external device (e.g., without external charger 203).

Cochlear implant 200 includes an implant body (main module) 210, a lead region 214, and an elongate intra-cochlear stimulating assembly 216. The implant body 210 generally comprises a hermetically-sealed housing 218 in which a stimulator unit (stimulation electronics) 222, a sound processor 224, an implant controller 226 (i.e., battery and power management component or battery processor), RF interface circuitry 228, and a rechargeable battery 230 are disposed. It is to be appreciated that cochlear implant 200 may include one or more other components that, for ease of illustration, have been omitted from FIG. 2A.

The implant body 210 also includes one or more implantable microphones 212 and an internal/implantable coil 232 that are each typically located external to the housing 218. The implantable coil 232 are connected to elements within the housing 218 via hermetic feedthroughs (not shown in FIG. 2). Implantable coil 232 is typically a wire antenna coil comprised of multiple turns of electrically insulated single-strand or multi-strand platinum or gold wire. The electrical insulation of implantable coil 232 is provided by a flexible molding (e.g., silicone molding), which is not shown in FIG. 2A. Generally, a magnet is fixed relative to the implantable coil 232 for magnetic coupling with a magnet in an external device.

Elongate stimulating assembly 216 is configured to be at least partially implanted in the recipient's cochlea (not shown) and includes a plurality of longitudinally spaced intra-cochlear electrical stimulating contacts (electrodes) 234 that collectively form a contact array 236 for delivery of electrical stimulation (current) to the recipient's cochlea. Stimulating assembly 216 extends through an opening in the cochlea (e.g., cochleostomy, the round window, etc.) and has a proximal end connected to the stimulator unit 222 via the lead region 214 and a hermetic feedthrough (not shown in FIG. 2). Lead region 214 includes one or more conductors (wires) that electrically couple the electrodes 234 to the stimulator unit 222. In this way, cochlear implant 200 electrically stimulates the recipient's auditory nerve cells, bypassing absent or defective hair cells that normally transduce acoustic vibrations into neural activity, in a manner that causes the recipient to perceive one or more components of the received sound signals.

The one or more implantable microphones 212 are configured to detect/receive input sound signals that are provided to the sound processor 224 by the RF interface circuitry 228. The sound processor 212 is configured to execute sound processing and coding to convert the received sound signals into output signals for use by the stimulator unit 222 in delivering electrical stimulation (current) to the recipient via electrodes 234.

The implantable coil 232 enables cochlear implant 200 to receive power/current signals from an external charger (e.g., external charger 103) via an RF link, sometimes referred to herein as an inductive power link, which is represented in FIG. 2A by arrow 242. The rechargeable battery 230 is configured to store the energy needed to power the other elements of the cochlear implant 200, as well as to provide the current needed to electrically stimulate the recipient's cochlea. The RF interface circuitry 228 is configured to operate under the control of the implant controller 226 and contains the necessary switches so as to charge the rechargeable battery 230 using the power received via inductive power link 242.

In general, conventional external chargers typically include a single transmit coil that is used to generate a magnetic field that is received at an implantable coil. In these conventional arrangements, when the emitted magnetic field passes through the implantable coil, a current is induced in the implantable coil that, in turn, can be used to charge a battery. The amount of current induced in the implantable coil is related to the total magnetic flux enclosed by the area of the implantable coil at a given time (i.e., the total magnetic flux linking a winding is proportional to the current through that winding). With a single transmit coil, so-called "dead" charging zones can be created when the total magnetic flux enclosed by the area of the implantable coil is zero. The total magnetic flux enclosed by the area of the implantable coil may be zero when the incoming and outgoing flux cancel each other, or when the magnetic field lines (of the magnetic field generated by the single transmit coil) cross parallel to the surface defined by the enclosed area of the implantable coil. The latter condition occurs when the implantable coil is placed orthogonal in the center of the external coil that emits the magnetic field. It is also the case that incoming and outgoing flux cancellation occurs for each point in space at specific angular orientations.

Even in conventional chargers with multiple external coil antennas, dead zones may still occur at specific orientation angles between the external coil antennas and an implantable coil. That is, in these conventional systems, no current is induced in an implantable coil when the implantable coil is disposed at specific orientations relative to the external coil antennas. These specific relative orientations may occur as a result of movement of the recipient relative to the external charger. For example, if the external charger is a pillow charger, the recipient may shift from side-to-side, roll over, etc., while sleeping. If the recipient takes a position where the implantable coil is oriented so that the magnetic flux through the implantable coil is zero, the battery within the recipient will not be charged.

Presented herein are techniques that attempt to account for movement of the recipient while his/her implant is being charged. In particular, an external charger in accordance with embodiments presented herein includes multiple coil antennas that are each configured to emit a magnetic field. The external charger is configured to manipulate the signals sent to each coil antenna to vary the relationship between the phases and/or amplitudes of the emitted magnetic fields such that the direction/orientation of the resulting combined/summed magnetic field vector (corresponding to the summation of the emitted magnetic fields) changes over time. Since the orientation of the combined magnetic field vector changes, the implantable coil will have a non-zero magnetic flux there through during different periods of time, regardless of the relative location of the implantable coil to the external coil antennas. Stated differently, by ensuring that the orientation of the summed magnetic field vector changes over time (e.g., the vector "moves" around), the locations of any dead charging zones will also change over time and the implantable coil will regularly have a non-zero magnetic flux there through that can induce a current in the implantable coil that, in turn, can be used to charge the battery in the implantable component. This arrangement provides implant recipients more freedom of movement, avoiding magnetic field orientations leading to dead charging zones.

Figure 2B:
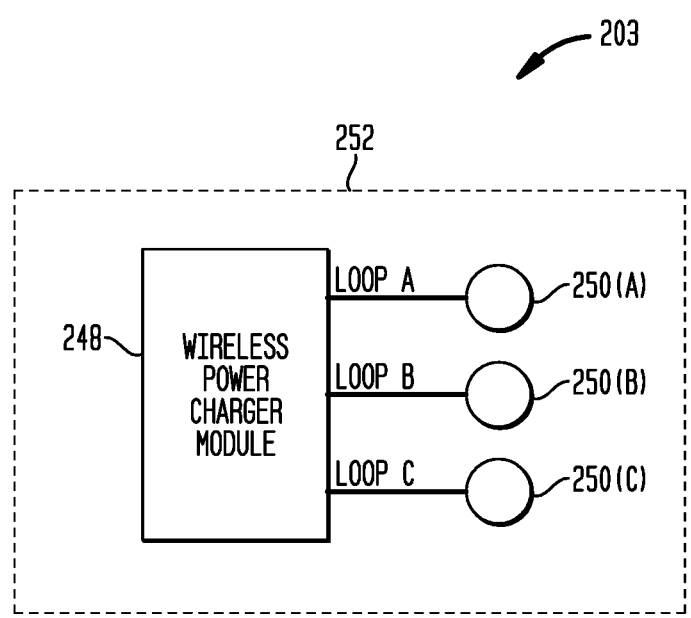
FIG. 2B is a block diagram of an external charging device, in accordance with embodiments presented herein.

FIG. 2B is a block diagram illustrating an arrangement for external charger 103, referred to as external charger 203, that is configured to account for movement of the recipient while his/her implant is being charged. FIG. 2C is a schematic block diagram illustrating further details of the external charger 203.

In the arrangement of FIGS. 2B and 2C, the external charger 203 is a so-called "pillow charger," that comprises a wireless power charger module, sometimes referred to herein as a coil excitation system, 248 and a plurality (i.e., two or more) of external loop or coil antennas 250 disposed in a pillow structure (pillow) 252. Although FIG. 2B illustrates a pillow charger 203, it is to be appreciated that the wireless power charger module 248 and the plurality of external coil antennas 250 may be integrated in other structures, such as a chair (e.g., relax chair), a mattress, a levitated cap, etc.

The pillow charger 203 comprises an electrical connection 254 to a power source. In one example, the electrical connection includes a galvanic isolation element 256 (i.e., a transformer) to insulate the power source from the electronics. The electrical connection 254 may also include a 12V DC adapter (not shown). The wireless power charger module 248 comprises a waveform generator 258 and three amplifiers 260(A), 260(B), and 260(C). In the illustrative embodiment of FIG. 2B, the plurality of coil antennas 250 comprise first, second, and third external coil antennas 250(A) (loop A), 250(B) (loop B), and 250(C) (loop C) that are each connected to the amplifiers 260(A), 260(B), and 260(C), respectively. A respective tuning capacitor 262(A), 262(B), and 262(C), and a respective transformer 264(A), 264(B), and 264(C) are connected between the amplifiers 260(A), 260(B), and 260(C) and the coil antennas 250(A), 250(B), and 250(C). The coil antennas 250(A), 250(B), and 250(C) are non-concentric (decentralized), but may have various relative positions and/or angles.

The wireless power charger 248 is configured to drive each of the coil antennas 250(A)-250(C) with different alternating current signals so that the coil antennas 250(A)-250(C) each emit a corresponding magnetic field. That is, the amplifiers 260(A), 260(B), and 260(C) connected to the waveform generator 258 provide energy to the corresponding coil antenna 250(A), 250(B), 250(C), which is placed in resonance with the corresponding tuning capacitor 262(A), 262(B), and 262(C). The transformers 264(A), 264(B), and 264(C) insulate the amplifiers 260(A), 260(B), and 260(C) and waveform generator 258 from the coil antennas 250(A), 250(B), 250(C), respectively. In addition, the transformers 264(A), 264(B), and 264(C) operate as current boosters, thereby avoiding the need for high voltages over the coil antenna 250(A), 250(B), 250(C). The high electrical current flowing in the secondary side of the transformers 264(A), 264(B), and 264(C) (and through the coil antennas 250(A), 250(B), 250(C)) generate three magnetic fields (i.e., the first coil antenna 250(A) emits a first magnetic field, the second coil antenna 250(B) emits a second magnetic field, and the third coil antenna 250(C) emits a third magnetic field).

As described further below, the wireless power charger module 248 is configured to drive one or more of the first, second, or third coil antennas 250(A), 250(B), or 250(C) so that at least one characteristic of the corresponding emitted magnetic field varies, over time, with respect to the same at least one characteristic of the one or of the other of the first, second, or third magnetic fields. By driving the coil antennas 250(A), 250(B), and 250(C) with different signals (e.g., having a non-fixed phase or amplitude relationship), the coil antennas are detuned from each other, thereby avoiding mutual influence. This is described further below with reference to FIGS. 3A and 3B.

Figure 3A:
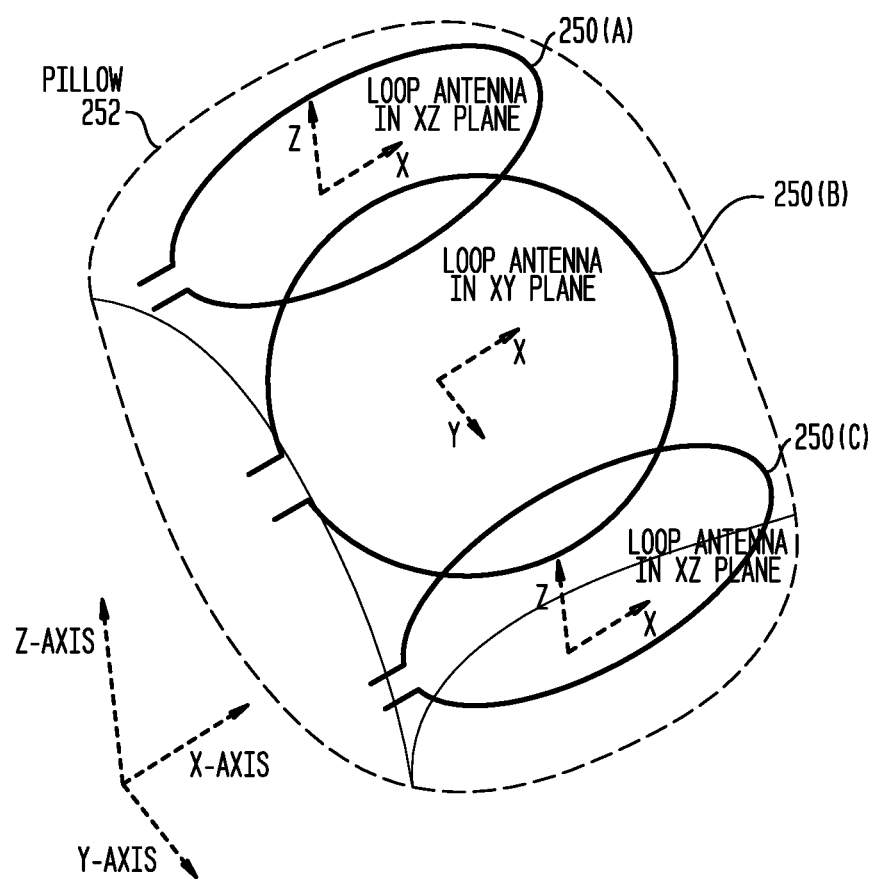
FIGS. 3A and 3B are schematic diagrams illustrating coil antennas of the external charging device of FIG. 2B.
Figure 3B:
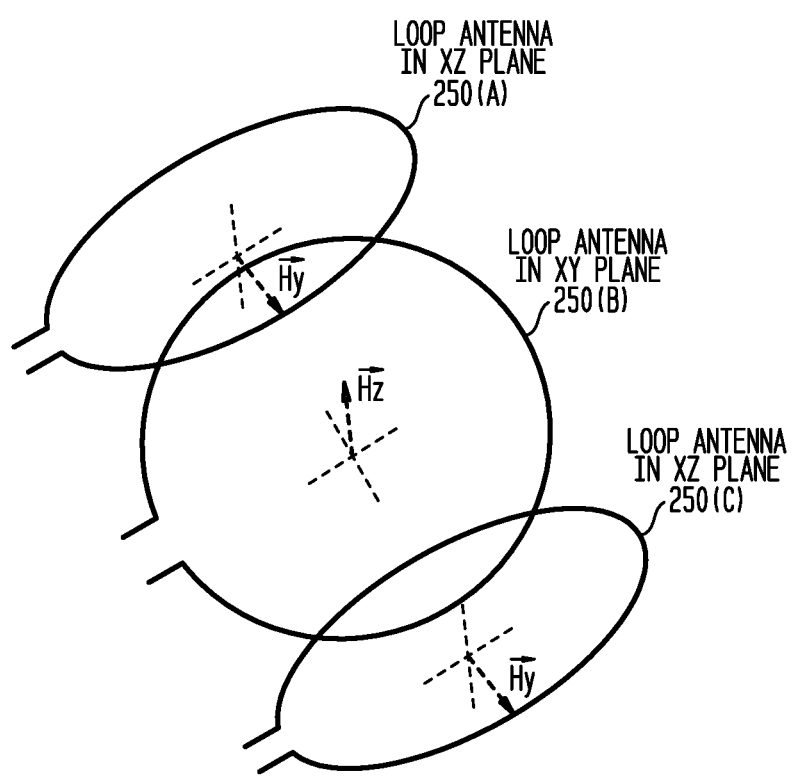

More specifically, FIGS. 3A and 3B are schematic illustrations of the coil antennas 250(A), 250(B), or 250(C) of pillow charger 203. For ease of illustration, FIGS. 3A and 3B are described with reference to a three-dimensional Cartesian coordinate system formed by three coordinate axis, referred to as the "X-axis," the "Y-axis," and the "Z-axis," which are each shown in FIG. 3A. In this arrangement, coil antennas 250(A) and 250(C) are disposed in the same plane, referred to herein as the XZ plane (formed by the X-axis and the Z-axis), while coil antenna 250(B) is disposed in a second plane, referred to herein as the XY plane (formed by the X-axis and the Y-axis).

As noted above, wireless power charger 248 drives each of the coil antennas 250(A), 250(B), or 250(C) with different alternating current signals so that the coil antennas 250(A)-250(C) each emit a corresponding magnetic field. A magnetic field is the magnetic effect of electric currents and magnetic materials and, at any given point in space, can be represented by a vector quantity. That is, there is both a direction associated with the field as well as a field strength. Therefore, as shown in FIG. 3B, the magnetic fields generated by coil antennas 250(A), 250(B), and 250(C) can be represented as magnetic field vectors Hx, Hy and Hz, respectively. Since coil antennas 250(A), 250(B), and 250(C) are in close proximity to one another, the magnetic field vectors (Hx, Hy and Hz) are summed as vector elements and this summed vector (i.e., the combined magnetic field vector) determines the magnetic flux that is received at the implantable coil (e.g., implantable coil 232). If the relative phases or amplitudes of the magnetic field vectors Hx, Hy and/or Hz vary over time, then the orientation/direction of the combined/summed magnetic field vector (i.e., the sum of Hx, Hy and Hz) will also fluctuate/change over time (e.g., rotates). Since the orientation of the combined magnetic field vector changes, the implantable coil 232 will have a non-zero magnetic flux there through during different periods of time, regardless of the relative location of the implantable coil 232 to the external coil antennas 250(A), 250(B), and 250(C). Stated differently, by ensuring that the orientation of the combined magnetic field vector changes over time (e.g., the direction of the vector "moves" around), the locations of the dead charging zones will also change over time and the implantable coil 232 will, at different times, have a non-zero magnetic flux there through that can induce a current in the implantable coil that, in turn, can be used to charge the battery 230 in the cochlear implant 200. This arrangement provides implant recipients more freedom of movement and leads to more reliable charging that is less dependent on head orientation.

Since the coil antennas 250(A), 250(B), or 250(C) have high Q-factors, the coil antennas could be detuned slightly from each other avoiding mutual influence. In certain arrangements, the coil antennas 250(A), 250(B), or 250(C) may also partially overlap in a common plane to limit and/or substantially eliminate mutual coupling between the coil antennas.

The relative phase or amplitude differences between two or more of the magnetic fields emitted by the coil antennas 250(A), 250(B), or 250(C) can vary continuously or discontinuously (e.g., randomly) to effectuate fluctuations/changes in the direction/orientation of the summed magnetic field vector. Continuously varying the phase of one or more of the phases of the magnetic fields emitted by the coil antennas 250(A), 250(B), or 250(C) can cause rotation in the orientation of the summed magnetic field vector.

Figure 4:
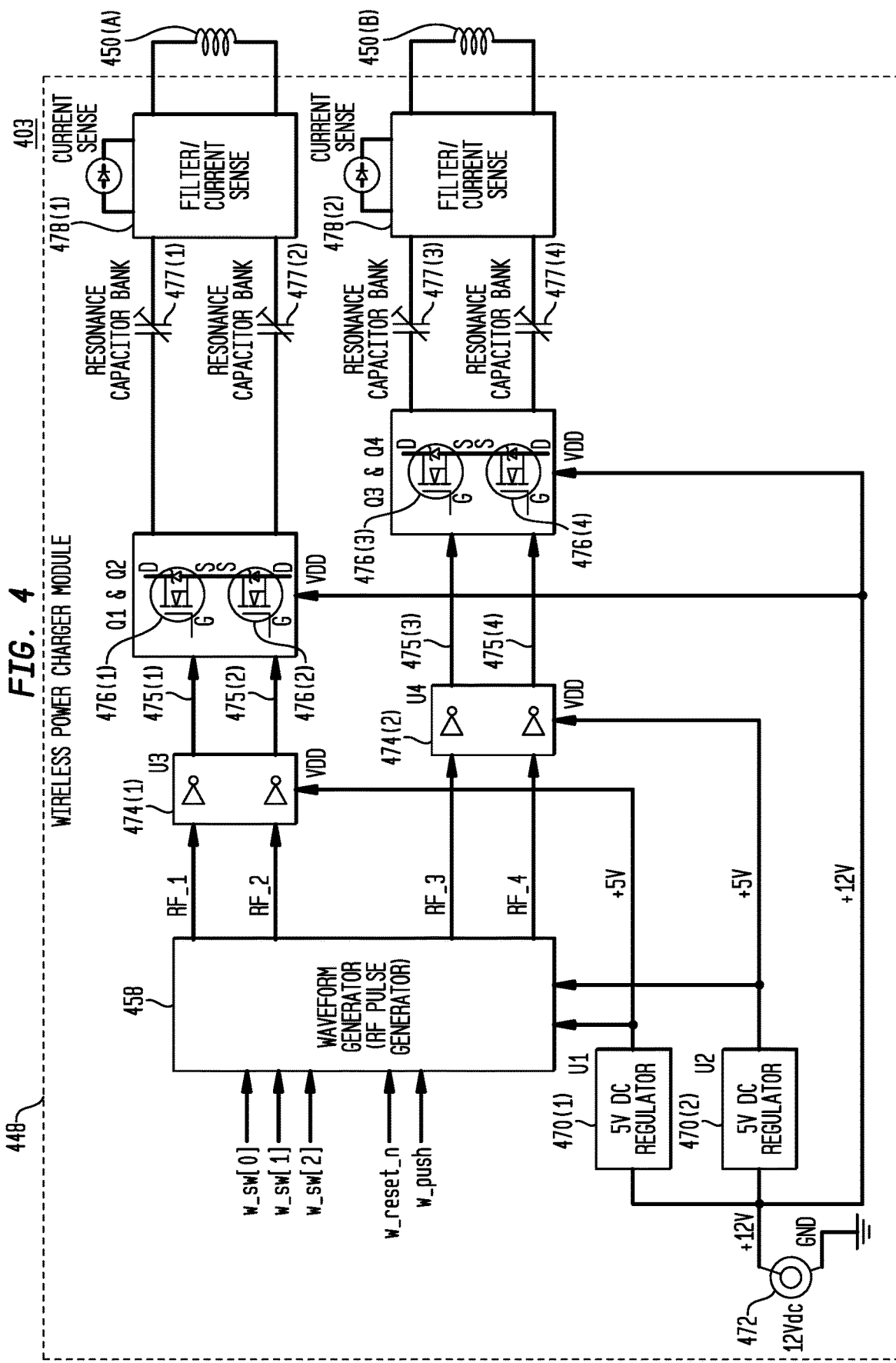
FIG. 4 is a block diagram of another external charging device, in accordance with embodiments presented herein.

As noted, FIGS. 2B, 2C, 3A, and 3B generally illustrate an example multi-loop external charger that includes three coil antennas. It is to be appreciated that the use of three coil antennas is illustrative and that other arrangements may include different numbers of coil antennas. For example, FIG. 4 is a schematic block diagram illustrating a multi-loop external charger 403 that includes two coil antennas 450(A) and 450(B) and a wireless power charger module 448.

In this example, the wireless power charger module 448 comprises a waveform generator (e.g., RF pulse generator) 458 with four outputs, labeled as RF_1, RF_2, RF_3, and RF_4. The wireless power charger module 448 also comprises two 5V voltage regulators 470(1) and 470(2) connected to a 12V DC adapter 472, inverting drivers 474(1) and 474(2), push-pull MOSFET power bridges 476(1), 476(2), 476(3), 476(4), and high-voltage capacitor banks 477(1), 477(2), 477(3), and 477(4). In certain examples, the wireless power charger module 448 also includes filter and current sense modules 478(1) and 478(2).

In operation, the waveform generator 458 generates alternating current signals to drive the two coil antennas 450(A) and 450(B). The inverting drivers 474(1) and 474(2) are used to boost these current signals to the appropriate MOSFET gate levels. The outputs of the inverting drivers 474(1) and 474(2), which are sometimes referred to herein as inverted RF outputs, are labeled in FIG. 4 as inverted RF outputs 475(1), 475(2), 475(3), and 475(4).

Figure 5:
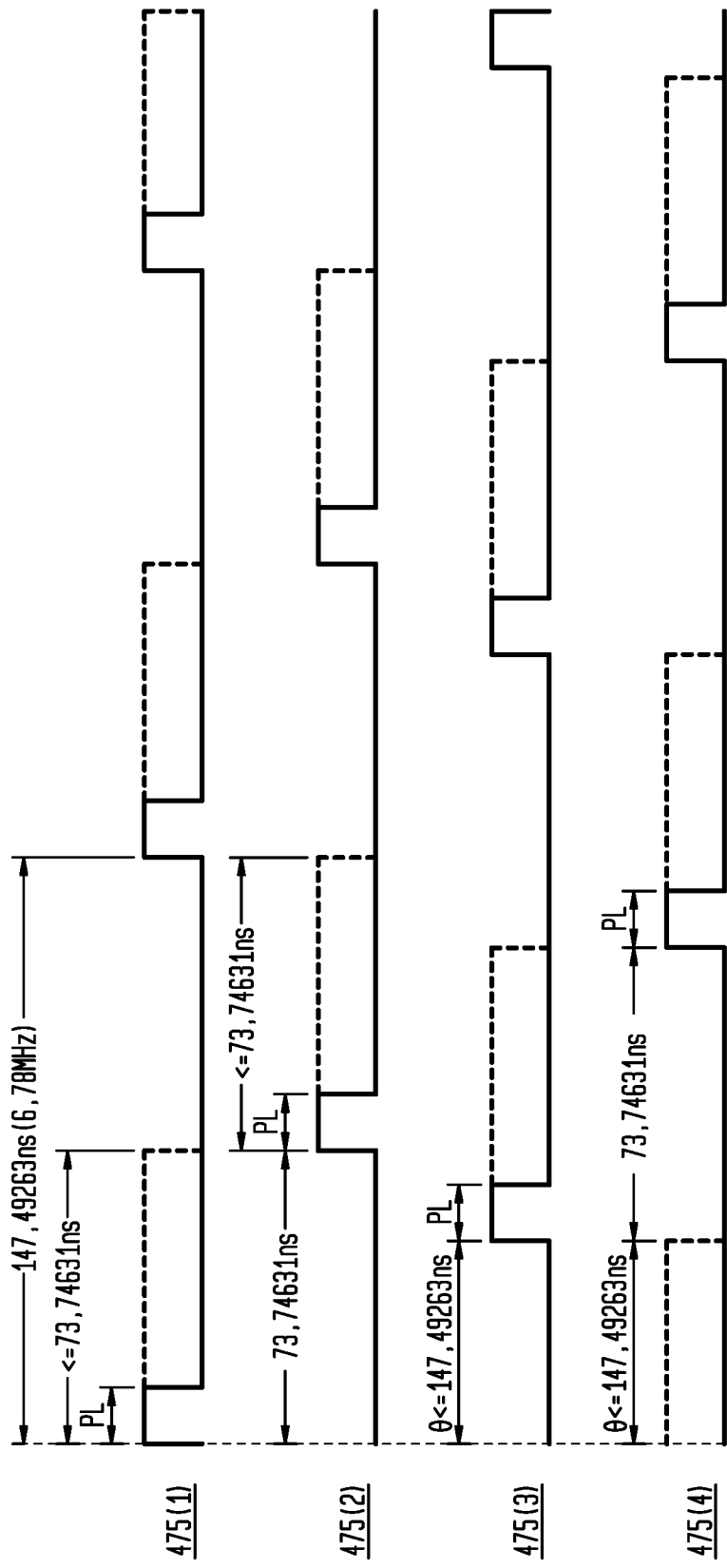
FIG. 5 is a diagram illustrating the generation of phase variations between two magnetic fields, in accordance with embodiments presented herein.

FIG. 5 is a timing diagram illustrating the four inverted RF outputs 475(1), 475(2), 475(3), and 475(4) for driving the four MOSFET's 476(1), 476(2), 476(3), 476(4) (2 half H-bridges). The pulses are generated at a frequency of 6.78 Mhz, but, as shown by the dashed lines in FIG. 5, the phase angle (θ) of the outputs provided to the second half H-bridge (i.e., outputs 475(3) and 475(4) delivered to MOSFET power bridges 476(3) and 476(4)) are slowly varying with respect to the outputs provided to the first half H-bridge (i.e., outputs 475(1) and 475(2) delivered to MOSFET power bridges 476(1) and 476(2)). That is, the dashed lines in FIG. 5 indicate that the pulse is continuously moving to the left or the right, meaning that the phase differences between the magnetic fields is continually varying. The pulses within each half H-bridge are non-overlapping.

As noted, FIG. 5 illustrates an example of variable phase (i.e., the phases of the emitted magnetic fields vary relative to one another). In alternative embodiments, the amplitudes of the magnetic fields may vary relative to one another. In such examples with variable relative amplitude, the width of the pulses change. For example, the width of the pulses change continuously, random pulses can be removed or added, etc.

As described above, in accordance with embodiments presented herein, one or more characteristics of the magnetic fields emitted by an external charger, such as chargers 203 and 403, are varied relative to one another. The magnetic field characteristics that may be varied relative to one another include, for example, the amplitudes and/or phases of the magnetic fields. In certain examples, an external charger has a plurality of different (e.g., eight) settings of the RF pulse width, which determines the amplitude of the magnetic fields. In the same or other examples, an external charger has a plurality of different (e.g., sixteen) modulation settings that control the speed at which the phase angle (θ) varies between two or more of the emitted magnetic fields.

In above embodiments, no communication between the external charger and the implantable component is needed (i.e. the charger operates in an "open-loop" configuration without feedback from the implantable component). However, in certain arrangements, the implantable component can be configured to send feedback to the charger. The implantable component can be configured to use load modulation (in the instance that the implantable component and charger are closely coupled), a wireless short range data link (e.g., a Bluetooth® link, a Bluetooth® Low Energy (BLE), etc.) or others forms of communication can be provided between the implantable component and the external charger to facilitate the communication of feedback (e.g. the voltage induced in the coil of the implantable component). Bluetooth® is a registered trademark owned by Bluetooth SIG, Inc. In such arrangements, the feedback can be used to optimize the relative variations (e.g., relative phase) between the magnetic fields emitted by an external charger to improve the battery charging process.

Figure 6A:
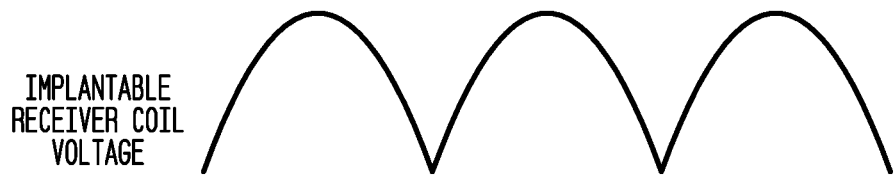
FIGS. 6A and 6B are diagrams illustrating voltages detected at an implantable coil, in accordance with embodiments presented herein.

More specifically, in the above examples the phases and/or amplitudes of the magnetic fields generated by external coil antennas of an external charger will vary over time relative to one another. As a result of this phase and/or amplitude variation, a voltage at the implantable coil of an implantable component will rise and fall as the external charger sweeps the relative phases and/or amplitudes of the external coil antennas. This rise and fall in the implantable coil voltage is shown in FIG. 6A. When the voltage falls below a certain level, useful received power may be lower at the implantable component such that the charging time of an implantable battery may be extended.

Figure 6B:
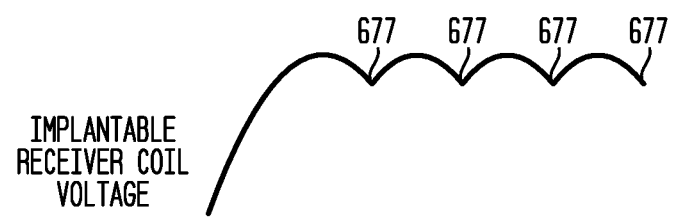

In accordance with certain embodiments presented herein, the implantable component may be configured to detect when the implantable coil voltage begins to drop/fall, for example, below a predetermined voltage level. In these embodiments, when the implantable component detects a drop in the implantable coil voltage (e.g., the voltage drops below a predetermined voltage level), the implantable component is configured to send a feedback signal to the external charger indicating that the implantable coil voltage has decreased to an unacceptable level. This feedback signal is sometimes referred to herein as a "field reversal" signal. In response to receipt of a field reversal, the external charger is configured to reverse the relative phase/amplitude changes between the magnetic fields of the external coil antennas. This is shown in FIG. 6B where an implantable component transmits a field reversal signal at points 677 (i.e., each time the implantable coil voltage decreases). By reversing the relative phase/amplitude changes each time the implantable coil voltage decreases, the orientation of a summed magnetic field vector is retained within a range that ensures that a useful amount of power is continuously received at the implantable component, which in turns leads to shorter battery charge times.

For example, the implantable component can be configured to detune the implantable coil (e.g., by changing the resonant characteristics of an associated circuit) to communicate field reversal signals to the external charger. This can be achieved without a separate data channel. In this example, the charger can be configured to reverse the field changes responsive to detecting a load modulation signal from the implantable component and to operate without feedback from the implantable component (i.e. in an "open-loop" configuration) in the absence of a discernable shift in load conditions (e.g., because the implantable coil has transitioned from the reactive near field to the far field and the external charger is no longer able to reliably detect load changes). That is, the system (implantable component and external charger) is configured to use load modulation when the position of the implantable coil (e.g. proximity to the charger coils) permits, and default to "open-loop" charging (i.e., without feedback from the implantable component) when the back link is unreliable or not discernable.

In certain embodiments in which more than two (2) external coil antennas are present, the external charger can sweep/vary the phase and/or amplitude of each coil antenna in turn. In such examples, when the external charger detects a field reversal signal from the implantable component, the external charger locks the phase/amplitude of the swept coil antenna and starts sweeping the phase and/or amplitude of the next coil antenna. In this way, the near-optimum phase/amplitude of each external coil antenna is achieved and regularly updated.

In certain arrangements that include more than two external coil antennas, it is possible that one or more external coil antennas will have little effect on the energy received at the implantable coil. In such arrangements, the implantable coil may be configured such that it does not detect, and/or does not signal to the external charger, voltage reductions associated with external coil antennas that have little effect on the energy received at the implantable coil. To prevent the system ending up in a deadlock, the external charger may be configured to sweep the amplitude and/or phase of an external coil antenna for a limited number of cycles before moving on to the next external coil antenna.

In certain embodiments, when a field reversal signal is detected, the external charger is configured to determine an optimal relative phase/amplitude difference between the magnetic fields that results in a maximum voltage at the implantable coil (i.e., a maximum amount of magnetic flux through the implantable coil). In these embodiments, the external charger may then adjust the amplitude/phase differences between the magnetic fields to achieve the maximum voltage at the implantable coil (e.g., instead of fixing the phase at the value when the charger receives the field reversal signal). The selected amplitude/phase differences may remain in place until a voltage reduction is detected at the implantable coil.

In certain embodiments, a charge power level optimization may be performed. More specifically, the minimum sufficient transmitted power level may vary significantly based on the distance between the external coil antennas and the implantable coil. The external charger may be configured to determine the minimum sufficient transmitted power level by: (1) determining the optimum coil phase/amplitude variation (as described above), (2) reducing the transmitted power level until no signal is received back from the implantable component, and (3) increasing the transmitted power by a pre-determined amount above the level found in step (2), above.

The use of the field reversal signals may make the system self-adjusting (e.g., when the implantable coil changes angle and therefore optimum transmit coil phase, this system will quickly adapt). In addition, at end of charge, the implantable component can minimize the received energy by sending the signal every time it detects the voltage rising. In addition, the required transmitted power level may be determined.

FIG. 7 is a flowchart of a method 780 for the wireless transfer of power from a wireless charger to an implantable component having an implantable coil, in accordance with embodiments presented herein. Method 780 begins at 782 where the wireless charger delivers a first alternating current signal to a first coil antenna of the wireless charger so as to produce a first magnetic field. At 784, the wireless charger delivers a second alternating current signal to a second coil antenna of the wireless charger so as to produce a second magnetic field, wherein the second alternating current signal causes at least one of the phase or amplitude of the second magnetic field to vary with respect to the phase or amplitude of the first magnetic field. At 786, an implantable coil receives a combined magnetic field comprised of the first and second magnetic fields, wherein the combined magnetic field generates an alternating current signal at the implantable coil.

Figure 8A:
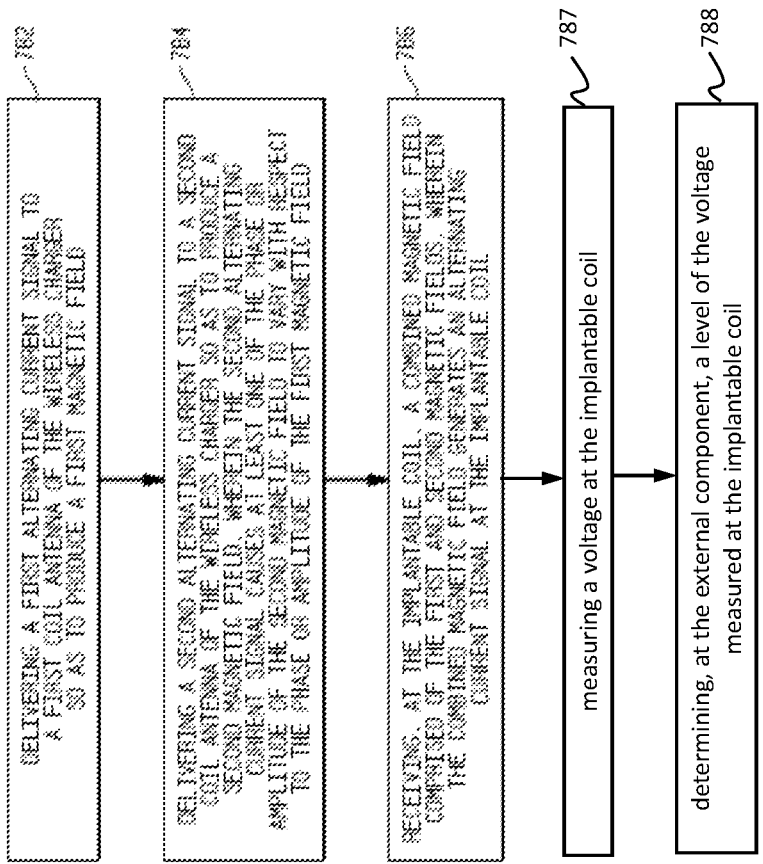
FIG. 8A is a flowchart of a method, in accordance with certain embodiments presented herein.

FIG. 8A is a flowchart of a method 880A, in accordance with certain embodiments presented herein. Method 880A includes the method 780 of FIG. 7, and further comprises, at 787, measuring a voltage at the implantable coil. At 788, method 880A further comprises determining, at the external component, a level of the voltage measured at the implantable coil.

Figure 8B:
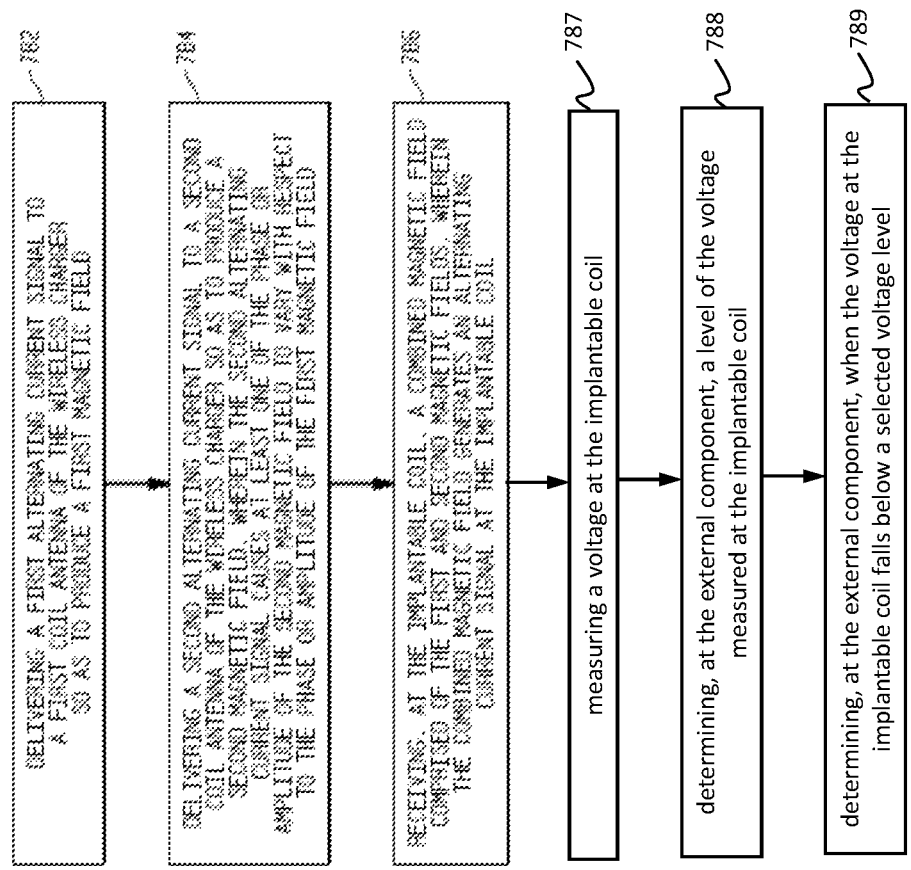
FIG. 8B is a flowchart of a method, in accordance with certain embodiments presented herein.

FIG. 8B is a flowchart of a method 880B, in accordance with certain embodiments presented herein. Method 880B includes the method 880A of FIG. 8A, and further comprises, at 789, determining, at the external component, when the voltage at the implantable coil falls below a selected voltage level.

Figure 8C:
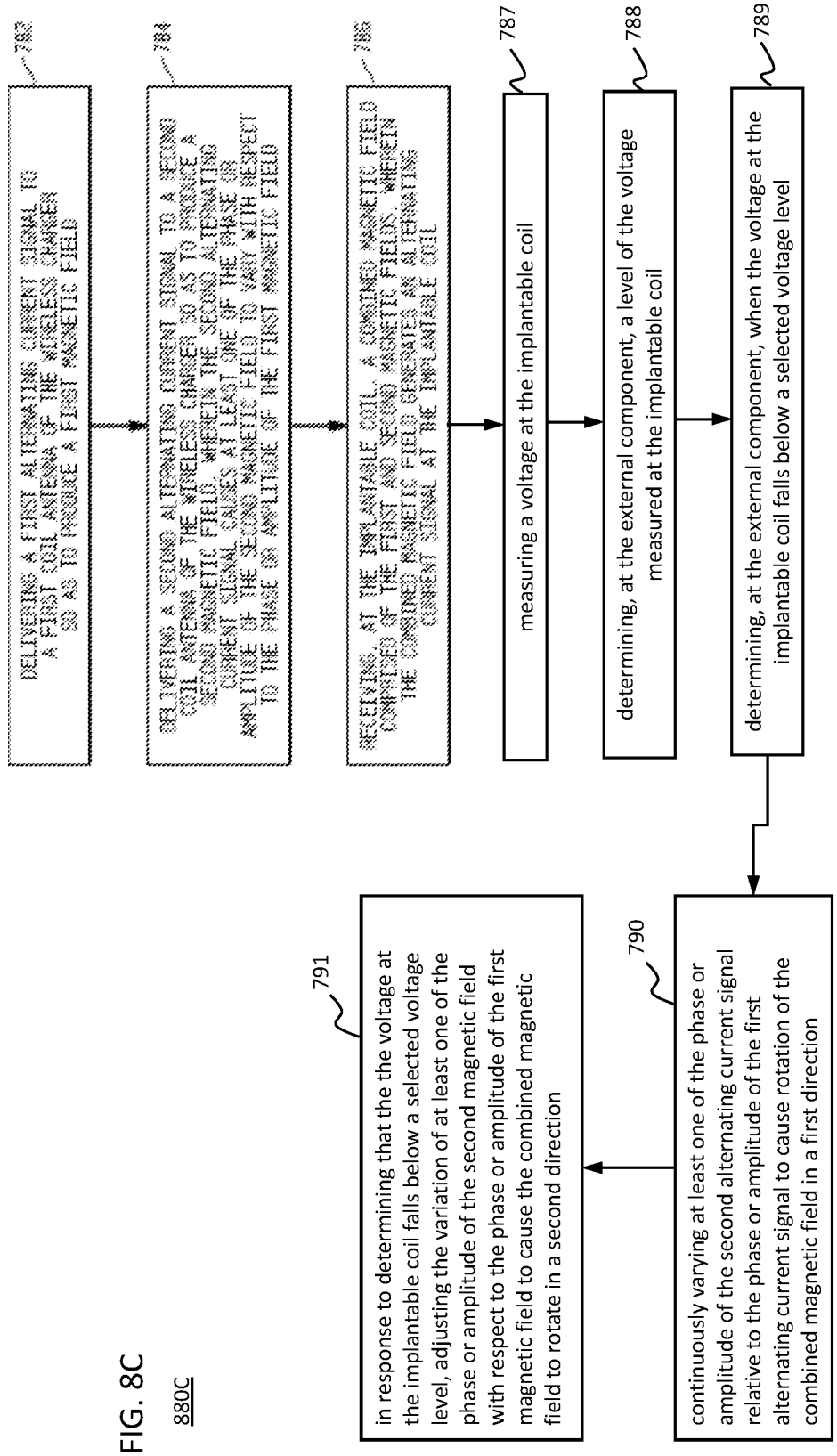
FIG. 8C is a flowchart of a method, in accordance with certain embodiments presented herein.

FIG. 8C is a flowchart of a method 880C, in accordance with certain embodiments presented herein. Method 880C includes the method 880B of FIG. 8B, and further comprises, at 790, continuously varying at least one of the phase or amplitude of the second alternating current signal relative to the phase or amplitude of the first alternating current signal to cause rotation of the combined magnetic field in a first direction. At 791, method 880C further comprises, in response to determining that the the voltage at the implantable coil falls below a selected voltage level, adjusting the variation of at least one of the phase or amplitude of the second magnetic field with respect to the phase or amplitude of the first magnetic field to cause the combined magnetic field to rotate in a second direction.

FIG. 8D is a flowchart of a method 880D, in accordance with certain embodiments presented herein. Method 880D includes the method 880A of FIG. 8A, and further comprises, at 792, determining, based on the voltage measured at the implantable coil, a relative phase or amplitude difference between the first and second alternating current signals that results in a maximum voltage at the implantable coil. At 793, method 880D further comprises adjusting a phase or amplitude of the second alternating current signal with respect to the phase or amplitude of the first magnetic field to generate a combined magnetic field that substantially produces the maximum voltage at the implantable coil.

FIG. 8E is a flowchart of a method 880E, in accordance with certain embodiments presented herein. Method 880E includes the method 880A of FIG. 8A, and further comprises, at 794, delivering a third alternating current signal to a third coil antenna of the wireless charger so as to produce a third magnetic field, wherein the third alternating current signal causes at least one of the phase or amplitude of the third magnetic field to vary with respect to the phase or amplitude of one or more of the first and second magnetic fields.

Although embodiments have been primarily described with reference to auditory prostheses, it is to be appreciated that the techniques presented herein may be implanted in other implantable medical devices.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for wireless transfer of power from a wireless charger to an implantable component having an implantable coil, the method comprising:

delivering a first alternating current signal to a first coil antenna of the wireless charger so as to produce a first magnetic field;

delivering a second alternating current signal to a second coil antenna of the wireless charger so as to produce a second magnetic field, wherein the second alternating current signal causes at least one of a phase or an amplitude of the second magnetic field to vary with respect to a phase or an amplitude of the first magnetic field;

receiving, at the implantable coil, a combined magnetic field comprised of the first and second magnetic fields, wherein the combined magnetic field generates an alternating current signal at the implantable coil;

continuously varying at least one of a phase or an amplitude of the second alternating current signal relative to a phase or an amplitude of the first alternating current signal to cause rotation of the combined magnetic field in a first direction; and measuring a voltage at the implantable coil induced by the combined magnetic field; and determining, at the wireless charger, when a level of the voltage measured at the implantable coil falls below a selected voltage level; and in response to determining that the voltage at the implantable coil falls below the selected voltage level, adjusting a variation between at least one of the phase or the amplitude of the second magnetic field with respect to the phase or amplitude of the first magnetic field to cause the combined magnetic field to rotate in a second direction.

2. The method of claim 1, wherein the second direction is substantially opposite to the first direction.

3. The method of claim 1, further comprising:

determining, based on the voltage measured at the implantable coil, a relative phase or amplitude difference between the first and second alternating current signals that results in a maximum voltage at the implantable coil; and adjusting a phase or amplitude of the second alternating current signal with respect to the phase or amplitude of the first alternating current signal to generate a combined magnetic field that substantially produces the maximum voltage at the implantable coil.

4. The method of claim 1, further comprising:

varying both the phase and amplitude of the second alternating current signal relative to the phase and amplitude, respectively, of the first alternating current signal.

5. The method of claim 1, further comprising:

delivering a third alternating current signal to a third coil antenna of the wireless charger so as to produce a third magnetic field, wherein the third alternating current signal causes at least one of the phase or amplitude of the third magnetic field to vary with respect to the phase or amplitude of one or more of the first and second magnetic fields.

6. The method of claim 5, wherein the first and second coil antennas are positioned within a first plane and the third primary coil is positioned in a second plane.

7. An external charger device for an implantable medical device comprising an implantable coil, the external charger device comprising:

at least first and second coil antennas configured to generate first and second magnetic fields, respectively; and a coil excitation system connected to the first and second coil antennas and configured to:
  independently drive the first and second coil antennas so that at least one characteristic of the first magnetic field varies, over time, with respect to the same at least one characteristic of the second magnetic field, wherein the first and second magnetic fields generate a combined magnetic field that induces a voltage at the implantable coil,
  monitor a level of the voltage induced the implantable coil, and
  determine, based on the level of the voltage induced the implantable coil, a relative difference between the at least one characteristic of the first magnetic field with respect to the same at least one characteristic of the second magnetic field that results in a maximum voltage at the implantable coil; and
  adjust the at least one characteristic of the first magnetic field with respect to the same at least one characteristic of the second magnetic field to generate a combined magnetic field that substantially produces the maximum voltage at the implantable coil.

8. The external charger device of claim 7, wherein the at least one characteristic comprises a plurality of characteristics, and wherein the coil excitation system is configured to independently drive the first and second coil antennas so that the amplitude of the each of the plurality of characteristic of the first magnetic field varies with respect to the second magnetic field.

9. The external charger device of claim 7, further comprising:
  a third coil antenna configured to generate a third magnetic field, wherein the coil excitation system is connected to the third coil antenna and configured to drive the third coil antenna so that at least one characteristic of the third magnetic field varies, over time, with respect to the same at least one characteristic of one or more of the first and second magnetic fields.

10. The external charger device of claim 9, wherein the first and second coil antennas are positioned within a first plane and the third coil antenna is positioned in a second plane.

11. The external charger device of claim 7, wherein the coil excitation system is configured to determine when the voltage at the implantable coil falls below a selected voltage level.

12. The external charger device of claim 11, wherein the coil excitation system is configured to continuously vary the at least one characteristic of the first magnetic field with respect to the same at least one characteristic of the second magnetic field to cause rotation of the combined magnetic field in a first direction; and
  in response to determining that the voltage at the implantable coil falls below a selected voltage level, adjust the variation of at least one characteristic of the first magnetic field with respect to the same at least one characteristic of the second magnetic field to cause the combined magnetic field to rotate in a second direction.

13. The external charger device of claim 12, wherein the second direction is substantially opposite to the first direction.

14. An implantable medical device system, comprising:
  an implantable component including an implantable coil;
  an external charger including:
    at least first and second external coil antennas in close proximity to one another and configured to emit first and second magnetic fields that collectively generate a combined magnetic field having a combined magnetic field vector; and
    a coil excitation system connected to the first and second coil antennas and configured to drive the first and second coil antennas with first and second time variant waveforms, respectively, to cause one or more of an amplitude or a phase of the first and second magnetic fields to vary relative to one another over time so as to cause rotation of the combined magnetic field vector;
  wherein the implantable component is configured to measure a voltage at the implantable coil, and
  wherein the coil excitation system is further configured to:
    determine a level of the voltage measured at the implantable coil,
    determine when the voltage measured at the implantable coil falls below a selected voltage level, and,
    in response to determining that the voltage measured at the implantable coil falls below the selected voltage level, adjust at least one characteristic of the first time variant waveform with respect to the same at least one characteristic of the second time variant waveform to cause the combined magnetic field to rotate in a second direction.

15. The implantable medical device system of claim 14, wherein the second direction is substantially opposite to the first direction.

16. The implantable medical device system of claim 14, wherein the coil excitation system is configured to:
  determine, based on the voltage measured at the implantable coil, a relative difference between at least one characteristic of the first and second time variant waveforms that results in a maximum voltage at the implantable coil; and
  adjust the at least one characteristic of the first time variant waveform with respect to the same at least one characteristic of the second time variant waveform to generate a combined magnetic field that substantially produces the maximum voltage at the implantable coil.

17. The implantable medical device system of claim 14, wherein the a coil excitation system is configured to vary both the phase and amplitude of the second alternating current signal relative to the phase and amplitude, respectively, of the first alternating current signal.

18. A method for wireless transfer of power from a wireless charger to an implantable component having an implantable coil, the method comprising:
  delivering a first alternating current signal to a first coil antenna of the wireless charger so as to produce a first magnetic field;
  delivering a second alternating current signal to a second coil antenna of the wireless charger so as to produce a second magnetic field, wherein the second alternating current signal causes at least one of a phase or an amplitude of the second magnetic field to vary with respect to a phase or an amplitude of the first magnetic field;
  receiving, at the implantable coil, a combined magnetic field comprised of the first and second magnetic fields, wherein the combined magnetic field generates an alternating current signal at the implantable coil;
  measuring a voltage at the implantable coil induced by the combined magnetic field; and
  determining, based on the voltage measured at the implantable coil, a relative phase or amplitude difference between the first and second alternating current signals that results in a maximum voltage at the implantable coil; and adjusting a phase or amplitude of the second alternating current signal with respect to the phase or amplitude of the first alternating current signal to generate a combined magnetic field that substantially produces the maximum voltage at the implantable coil.

19. The method of claim 18, further comprising:

varying both the phase and amplitude of the second alternating current signal relative to the phase and amplitude, respectively, of the first alternating current signal.

\* \* \* \* \*